United States Patent [19]

Baumgartner et al.

[11] Patent Number: 5,288,631
[45] Date of Patent: Feb. 22, 1994

[54] MASS TRANSFER MEMBRANE FOR OXYGENATION OF ANIMAL CELL REACTORS

[75] Inventors: Mark F. Baumgartner, St. Charles; William R. Tolbert, Manchester; John Shanahan, Florissant, all of Mo.

[73] Assignee: Centocor Incorporated, Malvern, Pa.

[21] Appl. No.: 822,353

[22] Filed: Jan. 17, 1992

Related U.S. Application Data

[63] Continuation of Ser. No. 534,125, Jun. 5, 1990, Pat. No. 5,112,760.

[51] Int. Cl.⁵ .............. C12N 5/00; C10J 1/08; B01D 33/70
[52] U.S. Cl. .............. 435/240.242; 435/240.241; 210/150; 261/122.1
[58] Field of Search ............ 210/150; 261/122, 75, 261/76, 77, 85, 87, 100; 435/284, 285, 313, 286, 240.24, 240.241, 240.242

[56] References Cited

U.S. PATENT DOCUMENTS

| | | | |
|---|---|---|---|
| 2,673,078 | 3/1954 | Simms | 261/76 |
| 3,997,396 | 12/1976 | Delente | 435/240.242 |
| 4,259,449 | 3/1981 | Katinger et al. | 435/240.25 |
| 4,391,912 | 7/1983 | Yoshida et al. | 435/240.25 |
| 4,537,860 | 8/1985 | Tolbert | 435/240 |
| 4,649,114 | 3/1987 | Miltenburger et al. | 435/240.25 |

FOREIGN PATENT DOCUMENTS 8824273  4/1990  United Kingdom ........ B01D 29/32

*Primary Examiner*—Michael G. Wityshyn
*Assistant Examiner*—Jane A. Williams
*Attorney, Agent, or Firm*—Morrison & Foerster

[57] ABSTRACT

A tubular membrane suitable for the delivery of a gaseous fluid to a surrounding medium has an irregular exterior surface to facilitate the diffusion of gas from the lumen to the exterior.

4 Claims, 2 Drawing Sheets

MASS TRANSFER MEMBRANE FOR OXYGENATION OF ANIMAL CELL REACTORS

This application is a continuation of application Ser. No. 07/534,125 filed, 5 Jun. 1990, now U.S. Pat. No. 5,112,760.

TECHNICAL FIELD

The invention relates to the provision of gas requirements in bioreactors. More specifically, it concerns effective apparatus and methods to provide oxygen or other needed gases for the culturing of cells or for other biological or chemical reactions.

BACKGROUND ART

In general, the growth and/or culture of animal cells, especially mammalian cells requires a constant supply of oxygen and effective removal of gaseous metabolic by-products, mainly carbon dioxide. The requisite gas exchange can be accomplished in a number of ways, including agitation of the reaction vessel and bubbling of oxygen-containing gases through the culture. In order for agitation to be effective, very low volumes of culture medium must be used since the effectiveness of this method depends on exposure of all of the cells in the culture to the surface. Bubbling of gases obviates this problem to some extent, but superimposes another wherein sufficient bubbling to be effective creates shear forces believed to be harmful to the relatively delicate animal cell membranes. Culture vessels, which specifically do not require agitation and provide the supply of oxygen through the use of gas bubbles, are, for instance, described in U.S. Pat. No. 4,259,449.

A different approach to the supply of needed oxygen and removal of gases is described in Miltenburger et al., U.S. Pat. No. 4,649,114, which describes the supply of oxygen and removal of carbon dioxide in a fermentation vessel for animal cells, especially insect cells, using a tube or hose of a synthetic polymer such as silicone rubber, laminated silicone rubber products, or a polytetrafluoroethylene (Teflon®) to provide the oxygen through diffusion. The tubes described by Miltenburger are required to be nonadherent with regard to the cells, thick enough to provide mechanical strength, and thin enough to permit oxygen to pass through readily. It is required that the oxygen be supplied *without* bubbling. The oxygen-dispensing tube is wound around a support in the illustrated embodiments and is stated to be successful in providing sufficient oxygen in the illustrated reaction vessels, which require agitation of the culture medium through mechanical or other means.

In variations of the method to supply oxygen through a membrane, the hollow fiber approach described in U.S. Pat. No. 4,391,912 evidently relies on the supply of oxygen along with culture medium which is provided through a closely spaced series of hollow fibers interspersed among the suspended cell culture. Similarly, U.S. Pat. No. 3,997,396 describes the supply of oxygen through a fiber to cells attached to its outer surface. In both of these cases, the proximity of the cells to be supplied oxygen to the membrane is relied upon to assure adequate transfer.

The continuous supply of medium and withdrawal of secreted products from animal cells cultured in an arrested state of proliferation and provision of oxygen through a tubular semipermeable membrane disposed throughout the culture medium is described in U.S. Pat. No. 4,537,860. The cell culture method described utilizes silicone rubber tubing, typically 1 mm inside diameter and 2 mm outside diameter, to supply oxygen to the culture. Again, sufficient surface area relative to the volume of the culture chamber must be assured so that all cells are proximal to the membrane.

Despite the successful operation of some of the culture methods described in the art, difficulty with providing an adequate supply of oxygen to desirably large volumes of cell culture remains. In general, it is found that the transfer of oxygen-containing gas from the interior of the supply tubular membrane to the culture medium is not as efficient as desired. This may be due in part to a limited surface area, but may also be due to other physical constraints such as an accumulated film-like barrier residing at the surface of the membrane. It is not clear which factors account for limitations on the capacity of the membrane to transfer oxygen to the cellular environment.

DISCLOSURE OF THE INVENTION

The invention provides a modified gas supply membrane which is particularly useful in the culturing of animal cells in suspension, or for cell culture in general, or for any biological or chemical reaction for which a constant supply of gas is required. The invention provides an irregular exterior surface on the membrane to expedite diffusion of gas into the surroundings which, in the case of culture medium, supports the growth and/or maintenance of animal cells at high densities.

Thus, in one aspect, the invention is directed to a method to culture animal cells which method comprises supplying a gaseous medium containing oxygen to the culture through a tubular membrane disposed throughout the culture, wherein the tubular membrane, has a fluted or otherwise irregular exterior surface. The remaining components of the culture medium, including nutrients or cofactors, can be supplied continuously or in a batch process by means generally known in the art. Similarly, removal of desired products, if required, may be continuous or by batch harvesting. The cells may either be capable of culture in suspension or may be anchorage dependent. In short, other aspects of the cell culture method of the invention are variable; however, the oxygen supply is effected through the tubular permeable membrane with irregular surface characteristics.

In another aspect, the invention is directed to a cell culture or other reaction chamber having disposed substantially throughout, a tubular membrane with a fluted or otherwise irregular outer surface at the exterior diameter.

MODES OF CARRYING OUT THE INVENTION

Various methods to culture animal cells have been described in the art as set forth in the background section above. In general, animal cells may be grown either in suspension or may require anchorage to a solid support, depending on the nature of the cell. Cells may be grown from an inoculum in a batch culture and the medium, after growth, may be harvested in order to obtain desired products, or the cells, themselves, may be the desired result of the culture. If secreted products are the purpose for culture of the cells, the cells may be first grown and then cultured without further significant proliferation, permitting the cells to utilize the nutrients provided to prepare the desired product. In this latter case, a continuous supply of nutrients and continuous withdrawal of conditioned medium may be advantageous.

Regardless of the purpose for cell culture (obtention of the cultured cells or manufacture of conditioned medium), and regardless of the approach (batch or continuous), and regardless of the nature of the cells (suspended or anchorage-dependent), an adequate and constant supply of oxygen is required. In the method of the invention, this supply is assured by introducing the gaseous oxygen-containing medium through the lumen of a tubular permeable membrane having a fluted or irregular surface at the outer diameter.

The tubular membrane is constructed of any material having sufficient permeability to oxygen and preferably having sufficient flexibility to be disposed through a culture medium. Suitable materials include rubber, silicone rubber, Teflon ®, and polyalkylenes. Particularly preferred is silicone rubber. In general, the dimensions of the tubular membrane can vary widely, the interior diameter being on the order of 0.5 mm–50 mm, and the exterior diameter being approximately 2 mm–5 mm greater than the inner diameter.

Although in a majority of applications the tubular membrane should be flexible, in some instances, flexibility is not required, and in these cases, other material such as porous ceramics, porous metals, or porous rigid plastics, may be used for construction. While the gas supply method is described for cell cultures, it can also be used for chemical reaction vessels or other processes conducted in liquid medium.

In the simplest embodiment, the interior surface of the tubular membrane is a regularly shaped circle (or ellipse or other ovoid), whereas the outer surface contains irregularities. In other embodiments, both the inner and outer surfaces contain similar or different irregularities.

Figure 1A:
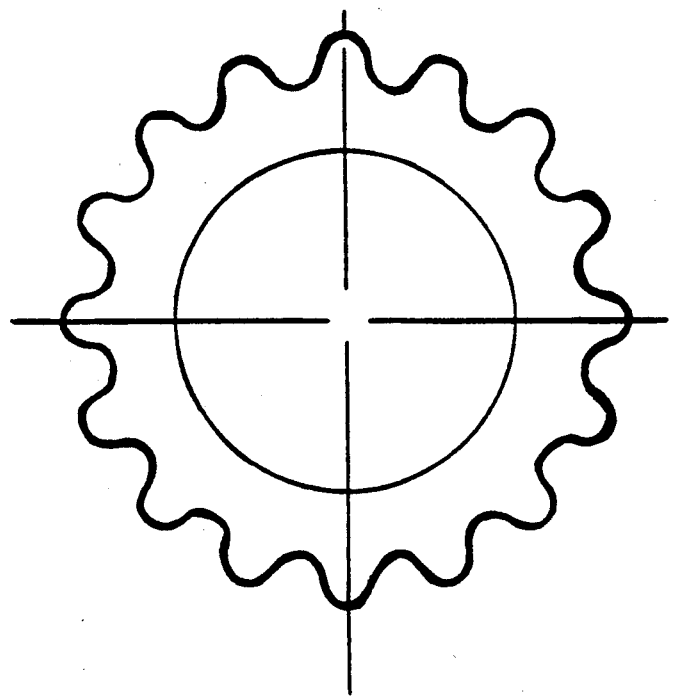
FIGS. 1A and 1B show cross sections of several typical embodiments of the tubular semipermeable membrane of the invention.
Figure 1B:
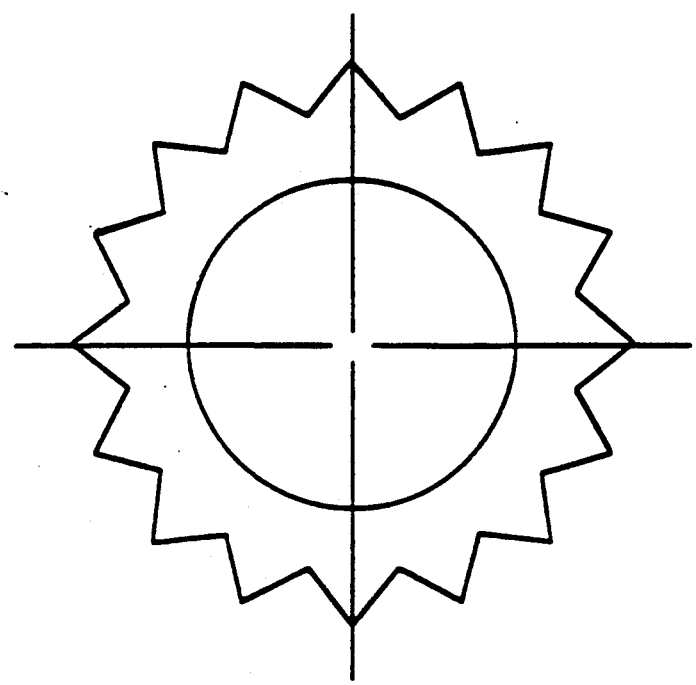

In one preferred embodiment, shown in FIG. 1A, the exterior surface contains longitudinally arranged flutes which are semicircular in cross section. In FIG. 1B, a similar preferred embodiment shows longitudinal triangularly cross-sectioned flutes. In other preferred embodiments, a spiral flute along the length of the tubing can be employed, or a granular set of irregularities can be superimposed on the outer surface. If longitudinal or spiral flutes are desired, the tubing can be made by extruding the material through a suitable die. For granular flutes, molding into a casting with the desired irregularities in negative image can be employed. Means to obtain the desired surface irregularities are known in the art generally.

In use, the predetermined length of tubular membrane having the required surface irregularities is disposed into the cell culture or other reaction chamber occupying positions of sufficient proximity to the volume of the reaction mixture or cell culture to assure that the gas penetrates satisfactorily into the medium. One end of the tubular membrane is connected to a source of oxygen or other process gas which allows access into the culture vessel or reaction chamber, and the other end of the membrane connected to an exhaust port from the vessel. The gas passes through the lumen of the tubing and the medium contacts the exterior walls thereof.

Gas is flowed through the tube which is in contact with the medium and exhausted through the downstream end, and is introduced at a pressure to maintain a satisfactory concentration of gas molecules throughout the traverse of the tubing. Flow rate is dependent on the length of tubing, the pressure of gas flowing into the tube, and an acceptable diffusion gradient throughout the length of the tube. The length of the tube is of any convenient length, but generally less than 5,000 feet. The flow rate of gas is limited by the characteristics of the material of which the membrane is made and the capacity of the connections to the gas supply to withstand pressure. The increased diffusion power of the fluted or otherwise irregular surface permits smaller pressures to be employed. Similarly, the geometry of the irregularities determines, in part, the mechanical strength of the tubing and the level of pressure which can be withstood.

Suitable reaction chambers include, in addition to mammalian or other animal cell cultures, bacterial fermenters and waste treatment.

EXAMPLES

The performance of standard tubing was compared with that of the fluted tubing of the invention using two 100 liter bioreactors culturing the same animal cell line in culture medium. Approximately 1000 feet of tubing was installed on support frame work and submerged below the culture level in each reactor. The standard tubing provided about 19,500 square centimeters of transfer area and the fluted tubing provided about 26,875 square centimeters of surface area. The transfer area provided by the fluted tubing was approximately 1.38 times greater than for the standard tubing.

Oxygen in a gas mixture was flowed through the lumen of the tubing at a concentration substantially higher than the dissolved $O_2$ concentration. Oxygen utilization was determined by the difference between inlet and outlet volume and $O_2$ concentration. The supply gas volume was approximately 300 cc of oxygen to maintain oxygen concentration in culture at 10 percent of atmoshperic. The results of the effectiveness of the fluted membrane are based on nearly equivalent supplies of oxygen for cell respiration and are correlated to a difference in gas pressures of 1.2 atmospheres. The fluted tubing was operated at a gauge pressure averaging 5 pounds per square inch and the standard tubing at a pressure averaging ⅜ pounds per square inch.

The reactor using standard tubing supported roughly $7 \times 10^6$ cells/ml for a packed cell volume of about 14 cc/l and consumed oxygen at 30 to 35 cc/min. An oxygen uptake rate in this range was the maximum capacity of supply gas.

The reactor having fluted tubing supported a cell population of $1.6 \times 10^7$ cells/ml for a packed cell volume of 33 cc/l. The oxygen demand was 77 cc/min, which was not the maximum available.

The maximum oxygen flow provided by the gas supply system attached to the tubing was 95% of 315 cc/min. For the standard tubing the 95% flow limit was reached at 30 to 35 cc/min. However, the fluted tubing demanded only 75% of the supply system oxygen limit to obtain the measured 77 cc/min uptake.

Thus, the standard tubing supported 320 cells/ml/$cm^2$ of membrane/atm of supply pressure. The fluted tubing supported 442 cells/ml/$cm^2$ membrane/atm supply pressure. The proportional increase in supported population is 1.38, identical to the surface area ratio; however the oxygen delivered by the fluted tubing was at least 2.2 times that of the standard tubing.

We claim:

1. An apparatus for conducting a biological or chemical reaction in liquid medium which comprises a vessel holding said medium, having disposed in said medium an integral tubular permeable membrane encompassing a lumen, the membrane having an interior surface and an exterior surface, the membrane suitable for the conduction of a gaseous fluid through the lumen, wherein said tubular membrane is characterized by an exterior surface having a routine pattern of irregularities in said surface.

2. The apparatus of claim 1 wherein the exterior surface is characterized by parallel semicircular flutes extending longitudinally along the tubular membrane.

3. The apparatus of claim 1 wherein the exterior surface is characterized by semicircular flutes extending spirally and longitudinally along the tubular membrane.

4. The apparatus of claim 1 wherein the interior surface is also irregular.

* * * * *